US00PP09211P

United States Patent [19]

Fryer

[11] Patent Number: Plant 9,211

[45] Date of Patent: Jul. 25, 1995

[54] SHRUB ROSE PLANT NAMED 'FRYTROOPER'

[75] Inventor: Gareth Fryer, Knutsford, England

[73] Assignee: Weeks Wholesale Rose Grower, Inc., Upland, Calif.

[21] Appl. No.: 185,707

[22] Filed: Jan. 24, 1994

[51] Int. Cl.[6] ..... A01H 5/00

[52] U.S. Cl. ..... Plt./1

[58] Field of Search ..... Plt. 1, 29, 28

*Primary Examiner*—Howard J. Locker

*Attorney, Agent, or Firm*—Christie, Parker & Hale

[57] ABSTRACT

A new variety of shrub rose suitable for garden decoration, having flowers of clear red coloration.

1 Drawing Sheet

BACKGROUND OF THE INVENTION

This invention relates to a new and distinct variety of shrub rose. The varietal denomination of the new variety is 'Frytrooper'. The plant is a bushy upright seedling cultivated for outdoor garden decoration. It has as its seed parent the variety 'Korlech' and as its pollen parent an unnamed seedling.

SUMMARY OF THE INVENTION

Among the features which distinguish the new variety 'Frytrooper' from other presently available and known commercial rose cultivars are the following combination of characteristics: its lasting bright red coloration, its prolific production of small flowers in large clusters and its attractive bushy fully branched habit. 'Frytrooper' may be asexually reproduced by cuttings, budding, grafting, layering and tissue culture.

Asexual reproduction of the new variety as performed by vegetative cuttings, grafting and budding in Kern County and Upland, Calif., shows that the foregoing and other distinguishing characteristics come true to form and are established and transmitted through succeeding propagations.

Comparison with Parent Varieties

The new rose may be distinguished from its seed parent, 'Korlech', by the following combination of characteristics: whereas 'Frytrooper' is classified as a shrub with proportionately small flowers and foliage, the seed parent is classified as a floribunda with significantly larger flowers and foliage. 'Korlech' bears flowers with 25 to 30 petals, whereas the new seedling bears flowers with significantly lower petalage.

The new variety may be distinguished from its pollen parent, an unnamed seedling, by the following combination of characteristics: whereas the unnamed pollen parent bears flowers of salmon orange coloration and 10 to 15 petals, 'Frytrooper' bears flowers of a bright red color with significantly more petals (18 to 22). The new variety produces a medium-tall plant with an upright bushy habit, whreas the pollen parent is of significantly shorter height and more rounded in its habit.

BRIEF DESCRIPTION OF THE ILLUSTRATION

The accompanying photograph illustrates the plant in color and shows the flowering thereof from bud to full bloom depicted in color as nearly correct as it is possible to make in a color illustration of this character. Throughout this specification, color values are described in accordance with the Colour Chart of The Royal Horticultural Society of London, England, except where common terms of color definition are employed.

DESCRIPTION OF THE NEW VARIETY

The following description is of rose plants of the new cultivar grown outdoors in Wasco, Calif. in the month of August. Phenotypic expression may vary with environmental, cultural and climatic conditions, as well as differences in conditions of light and soil.

FLOWER

The new variety bears its flowers usually several per stem. Flowers are borne in moderately large, irregular, rounded clusters on strong medium to long stems, about 16 to about 32 cm, for the class. Outdoors the plant blooms very abudantly and nearly continuously during the growing season. The flowers have no fragrance.

BUD

The peduncle is of average length for the class, about 4 to about 6 cm, of average to heavy caliper, and usually stiff. It is almost entirely smooth with few stipitate glands and hairs. Peduncle color is between 144A and 137B.

Before the calyx breaks, the bud is small to medium sized for the class about 1 cm at the widest point, moderately short in length, about 1.5 to about 2 cm, and somewhat pointed to broadly ovoid in shape. The surface of the bud bears some foliaceous appendages, stipitate glands and hairs usually with slender foliaceous parts extending beyond the tip of the bud equal to about one-half or more of its length. Bud color is between 144A and 137B sometimes with a slight blush on the side facing the sun of near 185A.

The inner surface of the sepals is covered with fine woolly tomentum; sepal margins are lined with few stipitate glands and several hairs.

As the petals open, the bud is moderately small, about 1 to about 1.5 cm wide, for the class, somewhat short to medium in length, about 2 cm, and somewhat pointed to braodly ovoid in form. The color of the outside surfaces of the newly opened petals is between 53A and 59A with a small basal attachment zone of near 2B. The color of the inside surfaces of the newly opened petals is between 59A and 46A wtih a basal attachment zone of similar size and coloration. The bud opens up well and is generally not prevented from opening by wet, cold, hot or dry weather.

BLOOM

When fully open, the bloom is moderately small to medium sized for the class, ranging from 4 to 6 cm. in diameter. Petalage is double with 18 to 22 petals and 3 to 5 or more petaloids arranged irregularly. When partially open, the bloom form is somewhat flat to cupped to globular, and the petals are moderately loosely cupped. When fully open, the bloom form is somewhat more flat to cupped and the petals are more loosely cupped to undulated with petal edges very slightly rolled outward.

PETALS

The petals are of very heavy substance and of medium thickness, with inside surfaces very velvety and outside surfaces moderately shiny to satiny. The outer petals are broadly obovate in shape with apices usually rounded. The inside petals are more narrowly obovate in shape with apices usually rounded.

NEWLY OPENED FLOWER

The outside surface of the outer intermediate and inner petals is between 53A and 59A with a small basal attachment zone of near 2C. The inside surface of the outer intermediate and inner petals is between 53A and 46A with a small basal attachment zone of near 2B.

The genral tonality of the newly opened flower is between 53A and 46A.

THREE-DAY-OLD FLOWER

The outside surface of the outer and inner petals is between 53A and 59B with a small basal attachment zone of near 4D. The inside surface of the outer and inner petals is between 53A and 46A with a basal attachment zone of similar size and coloration.

The genral tonality of the three day old flower is between 53A and 46A.

On the spent bloom, the petals usually drop off cleanly and are not particularly affected by cold, hot, wet or dry weather.

In August, blooms on the bush growing outdoors generally last from three to four or more days. Cut roses from plants grown outdoors and kept at normal indoor living temperatures generally last from three to four or more days.

MALE REPRODUCTIVE ORGANS

Stamens are average in number and are arranged regularly about the pistil; a few are mixed with petaloids. The filaments are of somewhat short to medium length, most with anthers. The anthers are moderately small for the class and all open approximately at the same time. Anther color is near 14 B when immature and near 166B at maturity. Pollen is somewhat jsparse and near 6C in color.

FEMALE REPRODUCTIVE ORGANS

Pistils are average in number (approximately 45). The styles are moderately uneven, short to average in length, average in caliper, and moderately loosely bunched. Stigma color is near 4C. Style color is near 6B. Ovaries are usually all enclosed in the calyx.

Hips have not been observed on this variety.

FOLIAGE

The compound leaves are usually comprised of three to seven leaflets and are borne abundantly. The leaves are moderately small, about 8 to about 13 cm in length and about 2.5 to about 5.5 cm in width, for the class, very heavy to crisp in texture, and semi-glossy to matte in finish. The leaflets are moderately small, about 5 to about 9 cm long and about 1.5 to about 3 cm wide, are shaped moderately ovoid to oval with somewhat acute apices and moderately round to acute bases. Their margins are usually simply serrate to irregular.

The upper surface of the mature leaf is between 137A and 136B. The under surface of the mature leaf is near 191B. The upper surface of the young leaf is between 137B and 136B, usually heavily suffused with near 183 A. The under surface of the yound leaf is near 183C.

The rachis is average in caliper and very smooth with few stipitate glands on the edges of the groove of the upper side. The under side of the rachis is very smooth with few stipitate glands and very small prickles.

The stipules are moderately long in length for the class with somewhat narrow to medium width and moderately long points that usually turn out at an angle of more than 45 degrees.

The plant displays an above average degree of resistance to powdery mildew and blackspot as compared to other commercial varieties grown under comparable conditions in Wasco, Calif.

GROWTH

The plant has a bushy, compact, upright, medium-tall habit, about 120 to about 150 cm, with very full branching. It displays very vigorous growth and the canes are of medium to heavy caliper for the class.

The color of the major stems are between 148A and 138B. They bear several large prickles which are moderately long for the class. The large prickles are almost straight hooked slightly downward with a very long somewhat narrow base; prickle color is near 177C. The major stems bear no small prickles and no hairs.

The color of the branches are between 146A and 136B. They bear several to many large prickles which are moderately long for the class. The large prickles are almost straight hooked slightly downward with a very long somewhat narrow base; prickle color is near 165B. The branches bear some small prickles of similar coloration and shape.

The color of the new shoots are between 146B and 137C moderately suffused with near 183C. They bear many large prickles which are moderately long for the class. The large prickles are almost straight hooked slightly downward with a very long somewhat narrow base; prickle color is near 183B. The shoots bear several small prickles of similar shape and coloration.

I claim:

1. A new and distinct variety of shrub rose plant substantially as described and illustrated herein.

* * * * *

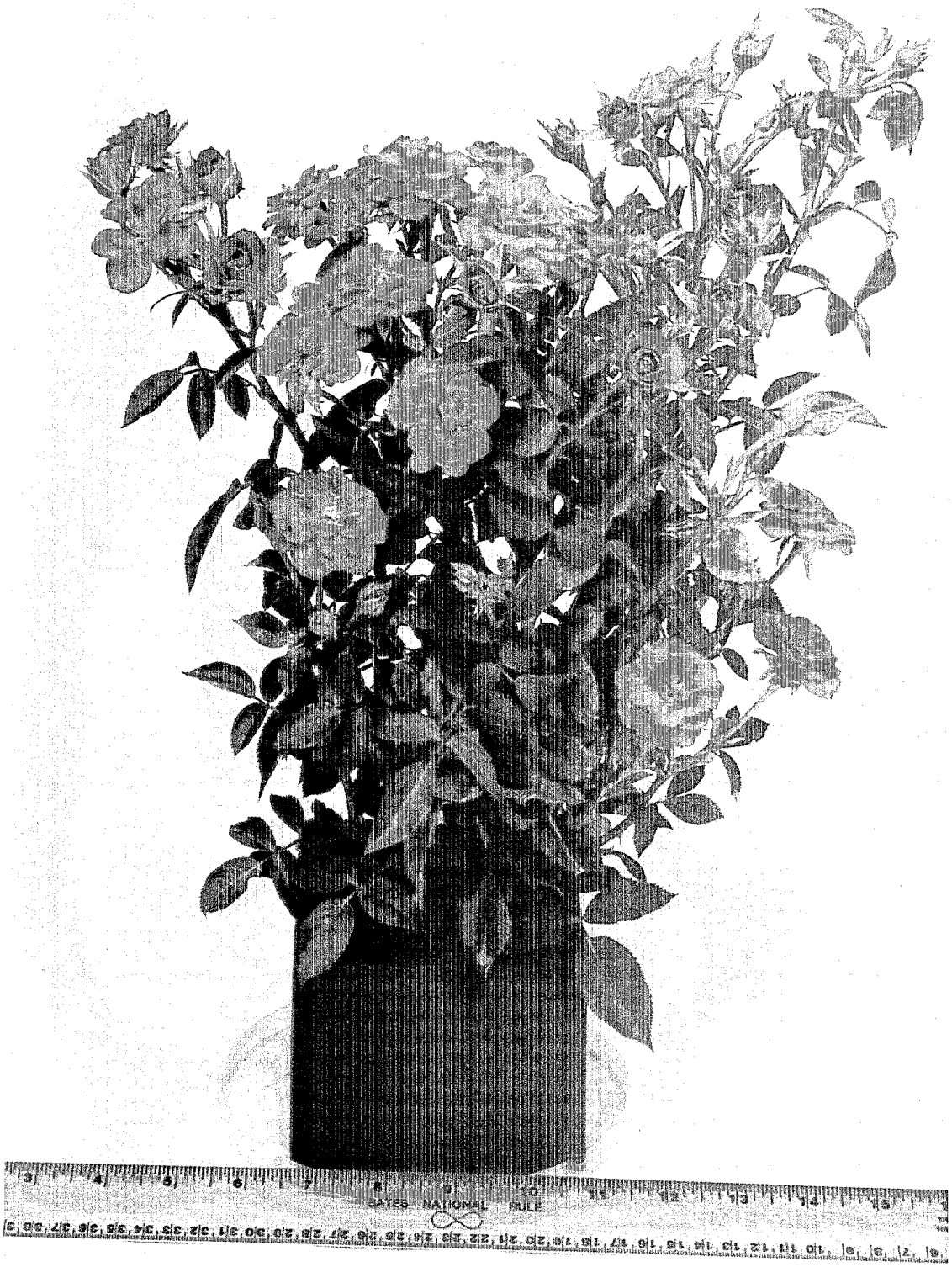
GATES NATIONAL RULE

UNITED STATES PATENT AND TRADEMARK OFFICE

CERTIFICATE OF CORRECTION

PATENT NO. : Plant 9,211

DATED : July 25, 1995

INVENTOR(S) : Gareth Fryer

It is certified that error appears in the above-indentified patent and that said Letters Patent is hereby corrected as shown below:

Column 1, line 41, change "whreas" to -- whereas --.
Column 2, line 17, change "abudantly" to -- abundantly --.
Column 2, line 43, change "braodly" to -- broadly --.
Column 3, line 29, change "genral" to -- general --.
Column 3, line 39, change "genral" to -- general --.
Column 3, line 56, change "14 B" to -- 14B --.
Column 3, line 57, change "jsparse" to -- sparse --.
Column 4, line 20, change "yound" to -- young --.

Signed and Sealed this

Thirty-first Day of October 1995

*Attest:*

Bruce Lehman

BRUCE LEHMAN

*Attesting Officer*

*Commissioner of Patents and Trademarks*